United States Patent [19]

Gumprecht et al.

[11] Patent Number: 4,967,024
[45] Date of Patent: Oct. 30, 1990

[54] CATALYZED HYDROFLUORINATION PROCESS

[75] Inventors: William H. Gumprecht, Wilmington, Del.; Wesley G. Schindel, Swedesboro, N.J.; Vinci M. Felix, Kennett Square, Pa.

[73] Assignee: E. I. Du Pont de Nemours and Company, Wilmington, Del.

[21] Appl. No.: 365,165

[22] Filed: Jun. 15, 1989

Related U.S. Application Data

[63] Continuation-in-part of Ser. No. 324,718, Mar. 17, 1989, abandoned, which is a continuation-in-part of Ser. No. 210,555, Jun. 23, 1988, abandoned.

[51] Int. Cl.$^5$ .............................................. C07C 17/08
[52] U.S. Cl. ..................................................... 570/168
[58] Field of Search ........................................ 570/168

[56] References Cited

U.S. PATENT DOCUMENTS 4,258,225  3/1981  Feiring ................................. 570/168

FOREIGN PATENT DOCUMENTS 0256146  2/1988  European Pat. Off. .
52-103392  8/1977  Japan .

OTHER PUBLICATIONS

A. E. Feiring, J. of Fluorine Chemistry, 13, pp. 7–18 (1979).

*Primary Examiner*—Alan Siegel

[57] ABSTRACT

Process of the preparation of highly fluorinated alkanes by contacting halogenated alkenes or alkanes with at least the molar equivalent of HF in the presence of a catalyst selected from TaF$_5$ and NbF$_5$ in an amount of at least 0.25 molar equivalent at a temperature of 0° C. to 175° C.

25 Claims, No Drawings

CATALYZED HYDROFLUORINATION PROCESS

CROSS REFERENCE TO RELATED APPLICATIONS

This application is a continuation-in-part of U.S. application Ser. No. 07/324,718 filed Mar. 17, 1989 now abandoned, which was a continuation-in-part of U.S. application Ser, No. 07/210,555 filed June 23, 1988 now abandoned.

FIELD OF INVENTION

Process for the preparation of highly fluorinated alkanes by contacting halogenated alkenes or alkanes with hydrogen fluoride (HF) in the presence of $TaF_5$ or $NbF_5$ and excess HF.

BACKGROUND OF INVENTION

A. E. Feiring, Journal of Fluorine Chemistry, 13, 7-18 (1979) discloses the use of tantalum pentafluoride as a catalyst for the addition of hydrogen fluoride to tetra- and trichloroethene and related compounds. The catalyst is also useful in fluorine-chlorine exchange reactions.

The use of tantalum pentafluoride as a catalyst for the addition of hydrogen fluoride to unsaturated compounds has been disclosed and claimed in Feiring, U.S. Pat. No. 4,258,225.

The need to provide economically attractive processes to convert certain halocarbon starting materials to highly fluorinated, hydrogen-containing alkanes useful as alternatives to current products for refrigerants, blowing agents, etc. has sparked interest in this area. The use of $TaF_5$ or $NbF_5$ under the conditions taught by Feiring, specifically as set forth in Column 1, Lines 62 to 63 of U.S. Pat. No. 4,258,225, requires "1 to 8 molar equivalents of HF and in the presence of 0.01 to 0.25 molar equivalents of $TaF_5$ or $NbF_5$ to produce a fluorinated alkane." These conditions are advantageous for addition of HF to the olefinic bonds of the starting halogenated alkenes, but are far less favorable to halogen exchange on the resulting adducts. Consequently, while highly fluorinated alkanes can be produced, the yields are too small for economically attractive production. In accordance with this invention it has been discovered that utilizing a combination of high specific catalyst loading plus a high ratio of catalyst and HF to halocarbon starting material enables the direct preparation of many highly fluorinated alkanes in economically attractive yields.

It is a particular object of this invention to provide a liquid-phase process for the preparation of 2,2-dichloro-1,1,1-trifluoroethane (HCFC-123) in high yields and with a low content of other isomers. Another object is to provide such a high yield, high purity $CF_3CHCl_2$ process which enables the use of relatively low HF concentrations, thereby minimizing HF-induced reactor corrosion and the need for high cost, high pressure equipment.

HCFC-123 is an environmentally-acceptable alternate to trichlorofluoromethane (CFC-11) as a blowing agent, solvent, tobacco puffing agent and refrigerant. HCFC-123 is also a useful raw material for preparing 2-chloro-1,1,1,2-tetrafluoroethane (HCFC-124) and pentafluoroethane (HFC-125) which are environmentally-acceptable products. HCFC-124 is useful as a blowing agent, sterilant carrier gas, propellant, refrigerant and raw material for preparing 1,1,1,2-tetrafluoroethane (HFC-134a) —a zero-ozone-depletion-potential replacement for dichlorodifluoromethane ($CFC_{12}$) as a refrigerant. HFC-125 is a zero-ozone-depletion-potential replacement for R-502 [an azeotropic blend of chlorodifluoromethane (HCFC-22) and chloropentafluoroethane (CFC-115)]. HFC-125 is also a useful raw material for preparing tetrafluoroethylene (TFE) and a long-term candidate replacement for HCFC-22.

SUMMARY OF THE INVENTION

This invention provides a process for preparing fluorinated alkanes of the formula $$R^1R^2R^3C-CR^4R^5R^6$$

wherein $R^1$, $R^2$, $R^3$, $R^4$, $R^5$ and $R^6$ are individually selected from H, F and Cl, wherein at least one of $R^1$, $R^2$ and $R^3$ is H, and at least one of $R^4$, $R^5$ and $R^6$ is F by contacting, at a temperature from 0° C. to 175° C. under substantially anhydrous conditions, one molar equivalent of a halogenated alkene of the formula $$R^1R^2C=CR^3R^4$$

wherein $R^1$, $R^2$, $R^3$ and $R^4$ are individually selected from H, F and Cl, with at least the stoichiometric molar equivalent of HF in the presence of at least 0.25 molar equivalent of at least one catalyst selected from tantalum pentafluoride ($TaF_5$) and niobium pentafluoride ($NbF_5$), with the proviso that the number of moles, x, of catalyst plus the number of moles, y, of HF, relative to the number of moles, z, of the halogenated starting material, are such that the total fluorine-to-starting material ratio, $(5x+y)/z$, equals at least $(6-w)$, preferably $(10-w)$ where w is the number of fluorine atoms in one mole of starting material.

This invention also provides for the preparation of the fluorinated alkanes described above, under substantially the same process conditions, utilizing a chlorinated alkane of the formula $$HR^1R^2C-CR^3R^4Cl$$

wherein $R^1$ and $R^2$ are individually selected from H and Cl, and wherein $R^3$ and $R^4$ are individually selected from H, Cl and F.

Utilizing substantially the same process conditions, this invention also provides for the preparation of fluorinated alkanes of the formula $$R^1R^2R^3C-CR^4R^5-CR^6R^7R^8$$

wherein $R^1$, $R^2$, $R^3$, $R^4$, $R^5$, $R^6$, $R^7$ and $R^8$ are individually selected from H, F and Cl, wherein at least one of $R^4$ and $R^5$ is H, and at least one of $R^6$, $R^7$ and $R^8$ is F, from an alkene of the formula $$R^1R^2R^3C-CR^4=CR^5R^6$$

wherein $R^1$, $R^2$, $R^3$, $R^4$, $R^5$ and $R^6$ are individually selected from H, F and Cl. It is preferred that $R^1$, $R^2$ and $R^3$ are individually selected from F and Cl, and that $R^4$, $R^5$ and $R^6$ be Cl. The fluorinated alkanes described above can also be prepared utilizing substantially the same process conditions from a chlorinated alkane of the formula $$R^1R^2R^3C-CR^4R^5-CR^6R^7R^8$$

wherein $R^1$, $R^2$, $R^3$, $R^4$, $R^5$, $R^6$, $R^7$ and $R^8$ are individually selected from H, F and Cl, with the proviso that at least one of $R^1$, $R^2$, $R^3$, $R^4$, $R^5$, $R^6$, $R^7$ and $R^8$ is Cl. It is preferred that $R^3$, $R^7$ and $R^8$ are Cl, $R^4$ and $R^5$ are F, and $R^6$ is H.

All the fluorinated alkanes produced in accordance with this invention are characterized by having at least one more, and preferably more than one more, fluorine atom than the halogenated alkene or alkane utilized as the starting material, and at least one of the fluorine atoms present in the fluorinated alkane so produced is the result of a halogen exchange reaction.

DETAILS OF THE INVENTION

In a typical embodiment of the invention which provides for fluorinated alkanes from halogenated alkenes having two carbons, the reaction proceeds as follows:

Addition of HF

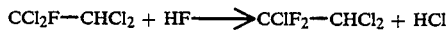

Halogen Exchange

Halogen Exchange

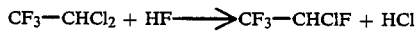

Halogen Exchange

Starting with the corresponding two carbon alkane the reaction proceeds as follows:

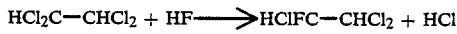

Halogen Exchange

Halogen Exchange

Halogen Exchange and Rearrangement

The degree to which the halogen exchange reactions proceed can be varied in accordance with this invention, particularly by varying the amount of HF and catalyst in combination as described herein below. To achieve the optimum degree of halogen exchange at least 0.25 molar equivalent of $TaF_5$ or $NbF_5$, or mixtures thereof and, preferably from 0.25 to 5.0 molar equivalents, based on the starting material, are required. The range of preference for effectiveness and economy is from 0.27 to 4.0 molar equivalents. The catalyst, preferably tantalum pentafluoride, is a commercially available crystalline solid and can be used alone or on a support such as carbon or fluorinated alumina.

In combination with the catalyst it is also necessary to utilize at least a specified minimum molar equivalent of HF, based on the halocarbon starting material, to achieve optimum halogen exchange and consequent high yields of highly fluorinated alkanes.

At relatively low catalyst concentrations, e.g., from 0.25 to about 0.5 mole per mole of starting material, the amount of HF will normally be greater than 8 moles per mole of starting material and can be as high as about 30 moles, preferably 15 to 30 moles per mole of the starting material. Fewer molar equivalents of HF, approaching the stoichiometrically required proportions, can be employed in conjunction with molar equivalents of catalyst greater than 0.5 mole per mole of starting material.

Thus, with tantalum pentafluoride at a concentration of 1 to 5 moles per mole of starting material, the amount of HF can be as low as the stoichiometric amount, provided that the concentrations of catalyst, HF and starting material are such as to constitute a high total fluorine to starting material ratio, as defined above. That is to say, when $(5x+y)$ is divided by "z", the quotient will equal at least $(6-w)$, preferably at least $(10-w)$, where "x" is the number of moles of tantalum pentafluoride, "y" is the number of moles of HF employed and "z" is the number of moles of the starting material to be fluorinated, and "w" is the number of fluorine atoms in the starting material.

Preferably, the relative proportions of the reactant materials will be such that the indicated ratio $(5x+y)/z$ is in the range of 15/1 to 35/1. Higher ratios provide little or no additional benefits. For example, in the manufacture of HCFC-123 from $CCl_2=CCl_2$ (wherein w=0 since there is no fluorine in the starting material) attractive results can be obtained with about 3 to 4 molar equivalents of $TaF_5$, the catalyst, in combination with as little as 3 to 4 molar equivalents of HF per mole of $CCl_2=CCl_2$, thereby greatly minimizing the problems of manufacture associated with the use of higher molar proportions of HF.

It should be noted that Ta and Nb pentachlorides are readily converted to the pentafluorides by reaction with HF under ambient conditions. Thus, the metal pentafluoride can be prepared for use in the process of the invention just prior to initiating the HF-starting material reaction for the preparation of the desired polyfluorinated organic product.

Under the preferred conditions of the invention, when the starting halogenated alkene or alkane is $Cl_2C=CCl_2$, $Cl_3CCHCl_2$, $CCl_2FCHCl_2$ or $CClF_2CHCl_2$, the favored product will be $CF_3CHCl_2$, and when the starting halogenated alkene or alkane is $Cl_2C=CHCl$, $FClC=CHCl$, $HCl_2CCHCl_2$, $HClFCCHCl_2$, $HF_2CCHCl_2$, $Cl_3CCH_2Cl$, $FCl_2CCH_2Cl$ or $F_2ClCCH_2Cl$, the favored product is $CF_3CH_2Cl$. When the starting halogenated alkene or alkane is $Cl_2C=CH_2$, $FClC=CH_2$ or $Cl_3C-CH_3$, the product can be $CFCl_2CH_3$, $CF_2ClCH_3$ and/or $CF_3CH_3$, depending on process conditions.

A variety of halogenated alkenes and halogenated alkanes, or mixtures thereof, may be utilized as starting materials in the practice of this invention. Preferred alkenes of the formula $R^1R^2C=CR^3R^4$ are wherein $R^1$ is H or Cl while $R^2$, $R^3$ and $R^4$ are Cl, or wherein $R^1$ and $R^2$ are H and $R^3$ and $R^4$ are Cl. The preferred halogenated alkanes of the formula $HR^1R^2C-CR^3R^4Cl$ are wherein $R^1$, $R^2$, $R^3$ and $R^4$ are Cl, wherein $R^1$ is H and $R^2$, $R^3$ and $R^4$ are Cl, or wherein $R^1$ and $R^2$ are H and $R^3$ and $R^4$ are Cl.

The specifically preferred halogenated alkenes and alkanes are $CCl_2=CCl_2$, $CHCl=CCl_2$, $CH_2=CCl_2$, $CCl_3CHCl_2$, $CHCl_2CHCl_2$, $CCl_3CH_2Cl$ and $CCl_3CH_3$.

In the production of $CF_3CHCl_2$ (HCFC-123) from any of the above precursors, it has been found that isomers of HCFC-123 are also formed in relatively high and objectionable amounts. The isomers consist mainly of $CClF_2CHClF$ (HCFC-123a) and lesser amounts of $CCl_2FCHF_2$ (HCFC-123b). It has also been found that the isomer content of the reaction product can be substantially reduced (to as low as non-detectable levels) when the products remain in contact with the reaction mass for a time sufficient to accomplish the desired low isomer result. By sufficient time is meant to include reaction time under autogenous pressure conditions and residence time under continuous process conditions wherein HF and the raw material are fed together to a liquid reaction mass containing metal pentafluoride and fluorination products of reaction, and the reaction product stream is continuously removed therefrom, with the reaction pressure maintained by controlling the amount of escaping gases. In such a process, residence time is determined by, and controlled by, the HF and starting material feed rates, the reaction temperature and pressure and the temperature of the gas leaving the reactor.

Anhydrous or substantially anhydrous conditions means that water, which is detrimental to the reaction, should be excluded as much as possible from the reaction zone. The HF which is commercially available can be used in the reaction directly. The halogenated alkenes and alkanes, and the catalysts also contain little or no water and can similarly be used directly. Exclusion of moisture from the reaction vessel by means of appropriate moisture traps, etc., is a routine procedure and is well known in the art.

The reaction can be carried out batchwise or in a continuous manner in the liquid phase at from 0° C. to 175° C., and preferably from 60° C. to 160° C. At reaction temperatures below these limits the reactions become too slow to be useful, and at temperatures above these limits the yields of products are lowered by side reactions and polymerization.

The reaction vessel is constructed from materials which are resistant to the action of hydrogen fluoride. Examples include stainless steels, high nickel alloys such as monel, "Hastelloy" and "Inconel", and plastics such as polyethylene, polypropylene, polychlorotrifluoroethylene and polytetrafluoroethylene. The high nickel alloys are preferred because of the superacidities of $TaF_5$ and $NbF_5$ in combination with liquid HF. For reactions at a temperature either below the boiling point of hydrogen fluoride (19.5° C.) or below the boiling point or the most volatile reactant, the reaction vessel can be closed or open to the atmosphere if provisions to exclude moisture are taken. For reactions at a temperature at or above the boiling point of hydrogen fluoride or the most volatile component, a closed vessel or a pressure-regulated partially open reactor is used to minimize the loss of reactants.

Pressure is not critical. Atmospheric and autogenous pressures are the most convenient and are therefore preferred. Means can be provided for the venting of the excess pressure of hydrogen chloride formed in the substitution reaction and can offer an advantage in minimizing the formation of side products.

In general, the reactions are conducted by introducing the reagents in any order into the reaction vessel. Generally, in batch-type autogenous pressure operation, the catalyst and starting material are placed in the reaction vessel which is then cooled, and the required amount of hydrogen fluoride is condensed in the vessel. The vessel may be cooled in Dry Ice or liquid nitrogen and evacuated prior to the introduction of hydrogen fluoride to facilitate the hydrogen fluoride addition. The contents of the vessel are raised to the appropriate reaction temperature and agitated by shaking or stirring for a length of time sufficient to cause the reaction to occur. The reaction times can be from 1 to 17 hours; the preferred reaction times are from 1 to 6 hours.

As indicated above, the fluorination reaction can be conducted in a continuous or semi-continuous manner with HF and the halocarbon starting material fed continuously or intermittently to a reaction vessel containing the Ta or Nb pentahalide at a temperature and pressure effective to result in the fluorination of the starting material to the desired polyfluorinated product. Preferably, the temperature and pressure are such that the desired product(s) is(are) in the gaseous state, so that a reaction product stream can be removed continuously or intermittently from the reaction zone. The pressure within the reactor can be controlled by means of a pressure regulator, and the temperature of the reaction product stream can be controlled, if desired, by use of a condenser/dephlegmator, all these techniques being well-known to the art.

It is convenient to initiate the HF-starting material reaction with the metal pentahalide in the presence of a diluent which may be a high-boiling inert liquid, e.g., a perfluorinated ether, or the desired reaction product itself, for example, HCFC-123 in the process for the manufacture of HCFC-123. When the available metal pentahalide is the pentachloride it is conveniently converted to the pentafluoride by treatment with HF and the removal of the hydrogen chloride by-product before initiating the reaction of HF with the halogenated starting material in the presence of the metal, preferably tantalum, pentafluoride.

The products are isolated by any of a variety of well-known techniques such as distillation or drowning into ice, washing with aqueous caustic, then water and drying with molecular sieves. A special isolation procedure involves scrubbing in 20.7% aqueous HCl precooled to −60° C. This permits collection of products boiling below ice temperature. The scrubbed products can be further purified by fractional distillation.

The highly fluorinated alkanes produced by the instant invention are useful as refrigerants, solvents and blowing agents. Those containing hydrogen are particularly useful in that they have reduced impact on the environment. They can also be used as starting materials for the preparation of other useful compounds.

EXAMPLES

In the following illustrative Examples all parts are molar proportions, and all temperatures are Centigrade. All reactions used commercial anhydrous HF and were carried out with the exclusion of water. The product mixtures were analyzed by Gas Chromatography (GC) and mass spectroscopy to identify the individual products. Analyses, where given, are in area percent unless otherwise indicated.

EXAMPLE 1

In a platinum-lined bomb were heated 0.036 mole of $TaF_5$, 0.097 mole of tetrachloroethylene and 2.0 moles of HF at 150° C. for 3 hours. The mole ratio of HF/tetrachloroethylene was 20.6 and of $TaF_5$/tetrachloroethylene was 0.37. While liquid organic products were not isolated in the scrubbing system, the off-gases contained 95.2% of $CF_3CHCl_2$, 1.4% of $CF_2ClCHCl_2$ and 0.9% of $CF_3CHFCl$.

EXAMPLE 2

The procedure of Example 1 was followed except that 0.100 mole of $CF_2ClCHCl_2$ was used instead of tetrachloroethylene. The mole ratio of $HF/CF_2ClCHCl_2$ was 20 and of $TaF_5/CF_2ClCHCl_2$ was 0.36. The off-gases contained 95.6% of $CF_3CHCl_2$, 1.7% of $CF_2ClCHCl_2$ and 0.9% of $CF_3CHFCl$.

EXAMPLE 3

In a stainless steel pressure vessel closed with a valve were stirred 0.072 mole of $TaF_5$, 0.175 mole of tetrachloroethylene and 3.93 moles of anhydrous HF while heating at about 108° C. for 2 hours. The mole ratio of HF/tetrachloroethylene was 22.5 and of $TaF_5$/tetrachloroethylene was 0.41. The cylinder was cooled to −70° C., and the HCl present was vented. The remaining volatiles were collected by vacuum-line transfer into a gas cylinder cooled to −70° C. while heating the pressure vessel. These volatiles were scrubbed in 20.7% aqueous HCl precooled to −60° C. and maintained near the temperature. The 17.0 g of colorless oil collected after scrubbing and water-washing contained 20.4% of $CF_3CHCl_2$, 0.6% of $CF_2ClCHClF$, 77.9% of $CF_2ClCHCl_2$, 0.5% of $CFCl_2CHCl_2$, and 0.2% of a mixture of $CF_3CHFCl$ and $CF_2ClCHF_2$.

EXAMPLE 4

The procedure of Example 3 was followed using 0.071 mole of $TaF_5$, 0.184 mole of tetrachloroethylene and 3.78 moles of anhydrous HF and reacting at about 130° C. for 2 hours. The mole ratio of HF/tetrachloroethylene was 20.5 and of $TaF_5$/tetrachloroethylene was 0.39. The 14.0 g of isolated organic liquid contained 64.7% of $CF_3CHCl_2$, 34.0% of $CF_2ClCHCl_2$, 0.3% of $CFCl_2CHCl_2$ and 0.3% of a mixture of $CF_3CHFCl$ and $CF_2ClCHF_2$.

EXAMPLE 5

The procedure of Example 3 was followed using 0.063 mole of $TaF_5$, 0.172 mole of pentachloroethane and 3.72 moles of anhydrous HF and reacting at about 110° C. for 2 hours. The mole ratio of HF/pentachloroethane was 21.6 and of $TaF_5$/pentachloroethane was 0.36. The 17.0 g of isolated organic liquid contained 15.4% of $CF_3CHCl_2$, 0.8% of $CF_2ClCHFCl$, 82.5% of $CF_2ClCHCl_2$, 0.5% of $CFCl_2CHCl_2$ and 0.5% of a mixture of $CF_3CHFCl$ and $CF_2ClCHF_2$.

EXAMPLE 6

The procedure of Example 3 was followed using 0.072 mole of $TaF_5$, 0.194 mole of tetrachloroethylene and 3.91 moles of anhydrous HF while heating at about 150° C. for 2 hours. The mole ratio of HF/tetrachloroethylene was 20.2 and of $TaF_5$/tetrachloroethylene was 0.37. The 10.0 g of isolated organic liquid consisted of 97.2% of $CF_3CHCl_2$, 1.2% of $CF_2ClCHCl_2$ and 1.0% of a mixture of $CF_3CHFCl$ and $CF_2ClCHF_2$.

EXAMPLE 7

The procedure of Example 6 was followed but with a different isolation technique. The mole ratio of HF/tetrachloroethylene was 19.8 and of $TaF_5$/tetrachloroethylene was 0.36. After the 2-hour reaction period at about 150° C., the volatiles in the pressure vessel were vented hot directly into 20.7% aqueous HCl at −50° C. The colorless liquid organic product collected, containing 97.0% of $CF_3CHCl_2$, was shown by infrared spectroscopy to contain a maximum of 1% of $CF_2ClCHFCl$.

EXAMPLE 8

The procedure of Example 3 was followed using 0.076 mole of $TaF_5$, 0.283 mole of as-tetrachloroethane ($CCl_3CH_2Cl$) and 3.96 moles of HF and reacting at about 85° C. for 2½ hours. The mole ratio of $HF/CCl_3CH_2Cl$ was 14.0 and of $TaF_5/CCl_3CH_2Cl$ was 0.27. The isolated organic products, which were gaseous above 15° C., consisted of 95.4% of $CF_3CH_2Cl$, 0.9% of $CF_2=CCl_2$ and 0.7% of $CCl_2=CHCl$.

EXAMPLE 9

The procedure of Example 3 was followed using 0.079 mole of $TaF_5$, 0.296 mole of trichloroethylene and 4.12 moles of HF and reacting at about 102° C. for 2 hours. The mole ratio of HF/trichloroethylene was 13.9 and of $TaF_5$/trichloroethylene was 0.27. The isolated volatile organic products, which were gaseous above 15° C., consisted of 95.2% of $CF_3CH_2Cl$, 0.1% of $CF_3CH_3$, 3.9% of $C_4H_3ClF_6$ isomers, and 0.1% of $C_3HClF_6$ isomers, and 0.4% of $C_5H_4F_6$ isomers.

EXAMPLE 10

Into a 150 ml. capacity stainless steel pressure cylinder was placed 0.093 mole of $TaF_5$. The cylinder was then closed with a valve, after which 0.366 mole of tetrachloroethylene and 3.698 moles of HF were added to the cylinder at about −70° C. and under vacuum. The cylinder was warmed to room temperature and then placed in a preheated oil bath. The contents of the cylinder were stirred magnetically and heated to the reaction temperature of over 15–20 minutes. The reaction proceeded at the reaction temperature, 143° C. to 150° C., for 2 hours, after which time the cylinder was cooled to about −70° C. Any contents of the cylinder which were not condensible at −70° C. (primarily HCl) were vented. The volatiles (organics plus unreacted HF) were then vacuum-line distilled out into a receiver cylinder at about −70° C. while heating the reaction cylinder to about 100° C. The volatiles were scrubbed in 20.7% aqueous HCl at about −50° C. The separated organic liquid was collected and dried over 4A molecular sieves. The organic liquid was analyzed by gas chromatography and mass spectroscopy, and the results are shown in Table 1. The residue in the stainless steel reaction cylinder was found to contain only recovered Ta compounds and corrosion products.

COMPARATIVE EXAMPLE 10A

The procedure of Example 10 was followed except that 0.034 mole of $TaF_5$, 0.383 mole of tetrachloroethylene, and 3.838 moles of HF were used. The results, shown in Table 1, reveal that the presence of high HF alone does not result in high yield of the desired highly fluorinated alkane, in this case 2,2-dichloro-1,1,1-trifluoroethane ($CF_3CHCl_2$).

TABLE 1

|  | Ex. 10 | Comp Ex. A |
|---|---|---|
| HF/PCE[1] Mole Ratio | 10.10/1 | 10.02/1 |
| TaF$_5$/PCE Mole Ratio | 0.25/1 | 0.09/1 |
| Volatiles (grams) | 134.82 | 138.79 |
| Reactor Residue (grams) | 21.5 | 9.81 |
| Recovery (%) | 97.5 | 99.2 |
| Organic Liquid (grams) | 48.1 | 51.84 |
| Analysis of Organic Liquid (area %) | | |

TABLE 1-continued

|  | Ex. 10 | Comp Ex. A |
| --- | --- | --- |
| $CF_3CHCl_2$ | 95.01 | 47.84 |
| $CF_2ClCHCl_2$ | 3.85 | 50.35 |
| $CF_2ClCHF_2$ | 0.17 | 0.07 |
| $CF_3CHFCl$ | 0.17 | 0.03 |
| $CF_3CH_2Cl$ | 0.58 | 0.67 |
| $CFCl_2CHF_2$ | 0.01 | 0.05 |
| $CF_2ClCHFCl$ | $ND^2$ | 0.46 |
| $CFCl_2CF_2Cl$ | 0.02 | 0.02 |
| $CCl_3CHF_2$ | ND | 0.06 |
| $CFCl_2CHCl_2$ | 0.04 | 0.24 |

[1]Tetrachloroethylene
[2]Not Detected.

EXAMPLE 11

In a dry 150 ml stainless steel cylinder equipped with a valved closure and containing a "Teflon" polytetrafluoroethylene-coated magnetic stirring bar was loaded, in a dry box under dry $N_2$, 225 g (0.815 mole) of $TaF_5$ (99% purity). The cylinder was closed, pressure-tested to 500 psig with $N_2$, cooled in Dry Ice-methanol and evacuated. To the cylinder were then added 39.7 g (0.239 mole) of tetrachloroethylene and 15.7 g (0.785 mole) of anhydrous HF. The cylinder was then closed, allowed to warm to room temperature and place in an oil bath preheated to 155° C. Magnetic stirring was started, and the reaction mixture was allowed to temperature-equilibrate for 30 minutes. With the oil bath at 149°–150° C., vapor samples were withdrawn from the reactor over a 120 minute period into 20.7% aqueous HCl precooled to about −50° C.

The organic liquids of these samples were drawn off, dried with molecular sieves and analyzed gas chromatographically to determine their composition. The analyses showed that, during the warm-up period, 85% of the tetrachloroethylene was converted to a mixture 5% by weight $CCl_2FCHCl_2$ (HCFC-121), 40% $CClF_2CHCl_2$ (HCFC-122) and 40% $CF_3CHCl_2$ (HCFC-123) containing 0.45% $CClF_2CHClF$ (HCFC-123a).

After 90 minutes at 149°–150°, the $CCl_2=CCl_2$ conversion was 96%, and the organic reaction products consisted of 2% $CCl_2FCHCl_2$, 18% $CClF_2CHCl_2$ and 76% $CF_3CHCl_2$ with its isomer, $CClF_2CHClF$, no longer detectable by gas chromatography. Little additional reaction occurred on continued heating of the reaction mixture. Apparently, the available HF had been consumed in the fluorination process and in the venting of the cylinder for sampling.

It will be noted that, in the above run, the $TaF_5/C_2Cl_4$ mole ratio is 3.41, the $HF/C_2Cl_4$ mole ratio is only 3.29 (about 10% excess over stoichiometric) and the total fluorine-to-$C_2Cl_4$ ratio is 5×0.815+0.785]/0.239 or 20.3. It is also noteworthy that, under these high fluorine-to-$C_2Cl_4$ conditions, $CF_3CHCl_2$ is obtained in good yield and substantially isomer-free.

EXAMPLE 12

A 13.5 gallon reactor, equipped with an agitator, a means for feeding HF and $CCl_2=CCl_2$, a condenser and a pressure-relief valve, was charged with 20.4 lbs. (0.057 lb-mole) of $TaCl_5$ and 40 lbs of 99.999% $CF_3CHCl_2$ as diluent during the initial stages of the reaction. The $TaCl_5$ was converted to $TaF_5$ by the addition of an excess of anhydrous HF at about 25° C. with stirring until HCl was no longer evolved.

The resulting $TaF_5/CF_3CHCl_2$ mixture was then heated with stirring to 125 and maintained at 125°–132° while simultaneously feeding HF at 2–4.5 lbs/hr. and $CCl_2=CCl_2$ at 3–8.5 lbs/hr. over a total reaction period of 150 hours. During this time the reactor pressure was varied from 360 to 465 psig and the condenser temperature from 80° to 100°. The above variations in the process conditions were employed to determine the effect of residence time on the yield and quality of the desired $CF_3CHCl_2$ product. The residence time of the reaction products in the reactor was varied during the run between 1.2 and 30.6 hours by varying the HF and $C_2Cl_4$ feed rates, the reaction temperature and pressure and the off-gas (condenser) temperature.

During the run, the vapor products exiting the reactor was sampled and analyzed gas-chromatographically for their contents of $CF_3CHCl_2$ (HCFC-123), $CClF_2CHClF$ (HCFC-123a) and $CCl_2FCHF_2$ (HCFC-123b), the isomer content being a measure of the quality of the HCFC-123 being produced. Table 2 presents the analytical results as a function of residence time in the order in which they were obtained.

TABLE 2

| Residence Time, Hrs. | % HCFC-123 | % HCFC-123a In Vapor | % HCFC-123b In Vapor |
| --- | --- | --- | --- |
| 3.0 | 82.3 | 2.7 | 0.41 |
| 1.2 | 34.8 | 13.4 | 0.41 |
| 18.7 | 97.8 | 0.07 | nil |
| 16.9 | 97.8 | 0.16 | nil |
| 14.5 | 98.4 | 0.07 | nil |
| 30.6 | 99.1 | 0.02 | nil |

The results show that, under the conditions of the continuous feed process, the longer the residence time, the lower the content of the unwanted isomers in the $CF_3CHCl_2$ product.

It will be appreciated that, in the above continuous feed process, both the $HF/C_2Cl_4$ mole ratio and the $TaF_5/C_2Cl_4$ mole ratio, although varied considerably during the run, were sufficiently high throughout the run to provide high total fluorine to $C_2Cl_4$ ratios well in excess of the required 10, with the result that $CF_3CHCl_2$ was produced in high yields. Furthermore, through control of residence time, the $CF_3CHCl_2$ could be obtained substantially free of its isomers.

EXAMPLE 13

The procedure of Example 12 was repeated, except that the quantity of $TaCl_5$ was more than doubled and corresponded to 0.135 lb-mole. Again, it was determined that the isomer production decreased with increasing residence time, and it was further found that increasing the $TaF_5$ loading shortened the residence time needed to produce $CF_3CHCl_2$ substantially free of its isomers.

What is claimed:

1. A liquid-phase process for the preparation of fluorinated alkanes of the formula

wherein $R^1$, $R^2$, $R^3$, $R^4$, $R^5$ and $R^6$ are individually selected from H, F and Cl, wherein at least one of $R^1$, $R^2$ and $R^3$ is H, and at least one of $R^4$, $R^5$ and $R^6$ is F which comprises contacting, at a temperature from 0° C. to 175° C. under substantially anhydrous conditions, one molar equivalent of a starting material selected from the group consisting of: (1) at least one halogenated alkene of the formula $$R^1R^2C=CR^3R^4$$

wherein $R^1$, $R^2$, $R^3$ and $R^4$ are individually selected from H, F, and Cl; or (2) at least one chlorinated alkane of the formula $$HR^1R^2C-CR^3R^4Cl$$

wherein $R^1$ and $R^2$ are individually selected from H and Cl, and wherein $R^3$ and $R^3$ are individually selected from H, Cl and F; with at least the stoichiometric molar equivalent of HF in the presence of at least 0.25 molar equivalent of at least one catalyst selected from tantalum pentafluoride (TaF$_5$) and niobium pentafluoride (NbF$_5$), with the proviso that the number of moles, "x", of catalyst plus the number of moles, "y", of HF, relative to the number of moles "z", of the halogenated starting material, are such that the total fluorine-to-starting material ratio, (5x+y)/z, equals at least (6-w) where "w" is the number of fluorine atoms in one mole of starting material so produce reaction products; removing said reaction products from contact with said catalyst and isolating a substantial yield of at least one fluorinated alkane having a substantially greater fluorine content than the starting material.

2. The process of claim 1 wherein the starting material is at least one compound selected from CCl$_2$=CCl$_2$, CHCl=CCL$_2$, CH$_2$=CCl$_2$, CCl$_3$CHCl$_2$, CCl$_3$CH$_2$Cl, CHCl$_2$CHCl$_2$ and CCl$_3$CH$_3$.

3. A liquid-phase process for preparing fluorinated alkanes of the formula $$R^1R^2R^3C-CR^4R^5-CR^6R^7R^8$$

wherein $R^1$, $R^2$, $R^3$, $R^4$, $R^5$, $R^6$, $R^7$ and $R^8$ are individually selected from H, F and Cl, wherein at least one of $R^4$ and $R^5$ is H, and at least one of $R^6$, $R^7$ and $R^8$ is F, which comprises contacting at a temperature from 0° C. to 175° C. under substantially anhydrous conditions, one molar equivalent of a starting material selected from the group consisting of: (1) at least one halogenated alkene of the formula $$R^1R^2R^3C-CR^4=CR^5R^6$$

wherein $R^1$, $R^2$, $R^3$, $R^4$, $R^5$ and $R^6$ are individually selected from H, F and Cl, or (2) at least one halogenated alkane of the formula $$R^1R^2R^3C-CR^4R^5-CR^6R^7R^8$$

wherein $R^1$, $R^2$, $R^3$, $R^4$, $R^5$, $R^6$, $R^7$ and $R^8$ are individually selected from H, F and Cl, with the proviso that at least one of the $R^1$, $R^2$, $R^3$, $R^4$, $R^5$, $R^6$, $R^7$ and $R^8$ is Cl; with at least the stoichiometric molar equivalent of HF in the presence of at least 0.25 molar equivalent of at least one catalyst selected from tantalum pentafluoride (TaF$_5$) and niobium pentafluoride (NbF$_5$) with the proviso that the number of moles, "x", of catalyst plus the number of moles, "y", of HF, relative to the number of moles, "z", of the halogenated starting material, are such that the total fluorine to starting material ratio, (5x+y)/z, equals at least (6-w) where "w" is the number of fluorine atoms in one mole of starting material to produce reaction products; removing said reaction products from contact with said catalyst and isolating a substantial yield of at least one fluorinated alkane having a substantially greater fluorine content than the starting material.

4. The process of claim 3 wherein, in the alkene starting material $R^1$, $R^2$ and $R^3$ are individually selected from F and Cl, and $R^4$, $R^5$ and $R^6$ are Cl.

5. The process of claim 3 wherein, in the chlorinated alkane starting material, $R^3$, $R^5$, $R^6$, $R^7$ and $R^8$ are Cl, and $R^4$ is H.

6. The process of claim 1 wherein the total fluorine to starting material ratio equals at least (10-w).

7. The process of claim 3 wherein the total fluorine to starting material ratio equals at least (10-w).

8. The process of claim 1 wherein the catalyst is present in an amount of 0.25 to 5.0 molar equivalents based on one molar equivalent of said starting material.

9. The process of claim 3 wherein the catalyst is present in an amount of 0.25 to 5.0 molar equivalents based on one molar equivalent of said starting material.

10. The process of claim 1 wherein the catalyst is present in an amount of 0.27 to 4.0 molar equivalents based on one molar equivalent of said starting material.

11. The process of claim 3 wherein the catalyst is present in an amount of 0.27 to 4.0 molar equivalents based on one molar equivalent of said starting material.

12. The process of claim 1 wherein the catalyst is tantalum pentafluoride.

13. The process of claim 3 wherein the catalyst is tantalum pentafluoride.

14. The process of claim 1 wherein the contacting temperature is from 60° C. to 160° C.

15. The process of claim 3 wherein the contacting temperature is from 60° C. to 160° C.

16. The process of claim 1 wherein the starting material is tetrachloroethylene, and a yield of CF$_3$CHCl$_2$ substantially free of isomers is obtained.

17. The process of claim 1 wherein the starting material is CF$_2$ClCHCl$_2$, and a yield of CF$_2$CHCl$_2$ substantially free of isomers is obtained.

18. The process of claim 1 wherein the starting material is CCl$_3$CHCl$_2$, and a yield of CF$_3$CHCl$_2$ substantially free of isomers is obtained.

19. The process of claim 1 wherein the starting material is tetrachloroethylene, and a yield of CF$_2$ClCHCl$_2$ substantially free of isomers is obtained.

20. The process of claim 1 wherein the starting material is pentachloroethane, and a yield of CF$_2$ClCHCl$_2$ substantially free of isomers is obtained.

21. The process of claim 1 wherein the starting material is as —tetrachloroethane and a yield of CF$_3$CH$_2$Cl substantially free of isomers is obtained.

22. The process of claim 1 wherein the starting material is trichloroethylene, and a yield of CF$_3$CH$_2$Cl substantially free of isomers is obtained.

23. The process of claim 1 wherein one molar equivalent of said starting material is contacted with up to about 30 moles of HF in the presence of 0.25 to about 5 moles of said catalyst.

24. The process of claim 1 wherein one molar equivalent of said starting material is contacted with at least 8 moles of HF in the presence of 0.25 to about 0.5 mole of said catalyst.

25. The process of claim 1 wherein one molar equivalent of said starting material is contacted with up to about 30 moles of HF in the presence of about 1 to about 5 moles of said catalyst and the total fluorine-to-starting material ratio equals at least (6-w).

* * * * *